United States Patent
Liu et al.

(10) Patent No.: US 10,877,015 B2
(45) Date of Patent: Dec. 29, 2020

(54) NON-INVASIVE DETECTING APPARATUS FOR FRUITS OR VEGETABLES, AND RANKING METHOD THEREOF

(71) Applicants: Mao-Cheng Liu, Taipei (TW); Jin-Cheng Lin, Taipei (TW); Jin-Liang Lin, Taipei (TW)

(72) Inventors: Mao-Cheng Liu, Taipei (TW); Jin-Cheng Lin, Taipei (TW); Jin-Liang Lin, Taipei (TW)

(73) Assignee: Jin-Cheng Lin, Taipei (TW)

( * ) Notice: Subject to any disclaimer, the term of this patent is extended or adjusted under 35 U.S.C. 154(b) by 130 days.

(21) Appl. No.: 15/995,178

(22) Filed: Jun. 1, 2018

(65) Prior Publication Data
US 2018/0348123 A1    Dec. 6, 2018

(30) Foreign Application Priority Data

Jun. 2, 2017    (TW) .............................. 106118334 A

(51) Int. Cl.
*G01N 33/02* (2006.01)
*G01N 1/44* (2006.01)
*G01N 21/84* (2006.01)

(52) U.S. Cl.
CPC .............. *G01N 33/025* (2013.01); *G01N 1/44* (2013.01); *G01N 21/84* (2013.01); *G01N 2021/8466* (2013.01)

(58) Field of Classification Search
None
See application file for complete search history.

(56) References Cited

U.S. PATENT DOCUMENTS

| | | | | |
|---|---|---|---|---|
| 5,164,795 A | * | 11/1992 | Conway | B07C 5/3422 250/226 |
| 5,808,305 A | * | 9/1998 | Leidecker | B07C 5/368 209/577 |
| 6,137,581 A | * | 10/2000 | Kimura | G01N 21/274 209/581 |
| 6,233,051 B1 | * | 5/2001 | Kimura | G01N 21/274 209/581 |
| 6,271,520 B1 | * | 8/2001 | Tao | B07C 5/342 250/330 |

(Continued)

*Primary Examiner* — Thomas R Artman
(74) *Attorney, Agent, or Firm* — Anna Tsang

(57) ABSTRACT

The invention provides a non-invasive detecting apparatus for fruits or vegetables, and ranking method thereof. The non-invasive detecting apparatus includes: a heater, configured to operably heat the fruits or the vegetables, by leaning the heater on a surface of the fruits or the vegetables; a temperature sensor, configured to operably sense a temperature variation level of the fruits or the vegetables, after heating the fruits or the vegetables by the heater; a processor, electrically coupled to the heater and the temperature sensor; a power supply, electrically coupled to the processor for supplying a power to the processor; and a user control unit, electrically coupled to the processor, for turning on, turning off, or setting the heater. According to the aforementioned temperature variation level, a ranking method for the non-invasive detecting apparatus for fruits or vegetables includes: a lowest temperature variation level corresponds to a highest sweetness, and a highest temperature variation level corresponds to a lowest sweetness.

11 Claims, 3 Drawing Sheets

(56) References Cited

U.S. PATENT DOCUMENTS

| | | | | |
|---|---|---|---|---|
| 6,563,579 B1* | 5/2003 | Kimura | ............... | G01N 21/274 356/246 |
| 6,610,953 B1* | 8/2003 | Tao | ........................ | B07C 5/342 209/11 |
| 6,754,600 B2* | 6/2004 | Hashimoto | ............ | G01N 21/31 250/339.01 |
| 7,173,246 B2* | 2/2007 | Benedetti | ............. | G01N 21/255 250/358.1 |
| 2002/0161540 A1* | 10/2002 | Hashimoto | ............ | G01N 21/31 702/81 |
| 2018/0348123 A1* | 12/2018 | Liu | ................... | G01N 21/3563 |

\* cited by examiner

NON-INVASIVE DETECTING APPARATUS FOR FRUITS OR VEGETABLES, AND RANKING METHOD THEREOF

CROSS REFERENCE

THE PRESENT INVENTION CLAIMS PRIORITY TO TW106118334, FILED ON Jun. 2, 2017.

BACKGROUND OF THE INVENTION

Field of Invention

The present invention relates to a non-invasive detecting apparatus for fruits or vegetables, and a ranking method thereof. Especially, the non-invasive detecting apparatus and the ranking method are capable of detecting a sweetness of the fruits or vegetables in a non-invasive detecting step, with no cut on or destruction of the fruits or the vegetables.

Description of Related Art

For the fruits or vegetables for sale at market, a quality detection is generally based on a visual method of checking appearance, shape, size, color, and gloss of the fruits or the vegetables, for ranking the fruits or the vegetables. However, some factors possibly influencing the quality of the fruits or the vegetables, such as sweetness, sour grade, contents of amino acid and vitamins, cannot be analyzed by the visual method. Until now, there is no suitable detecting technology of these above-mentioned factors (ex: sweetness) for the fruits or vegetables in the market.

Generally speaking, the sweetness of the fruits or the vegetables is susceptible to multiple factors such as harvesting period, fertilization management, blossom and fruit thinning (to thin the fruits is to get rid of the small ones and give those leave on the tree a better chance to grow bigger), grafting, and so on. Besides, the compositions of the fruits or the vegetables, such as moisture, sweetness and so on, are different from one another, so that the flavors of the fruits or the vegetables are different. Therefore, when the grade or the price of the fruits or the vegetables is determined by the visual method, it cannot correctly judge the sweetness of the fruits or the vegetables. The visual ranking method possibly wastes a lot of manpower, and causes a big difference between the determined sweetness and the exact sweetness. This considerable difference further brings farmers, related supply chains, and consumers a lot of problems.

In recent years, an invasive (destructive) detecting method is introduced for detecting the sweetness of fruits or vegetables. The system and detecting steps related to this detecting method are complicated and expensive, wherein the necessary cost is around several million dollars. Besides, this technology is unable to have an instant detecting result, so that it is not practical. Further, it has an important drawback that cannot serve non-invasive detecting purpose. Therefore, for farmers of the fruits or the vegetables, this invasive detecting method does not meet their requirements and its application is limited.

Furthermore, for farmers of the fruits or the vegetables, the sweetness of the fruits or the vegetables after harvest is very important. However, how to ensure the sweetness of the fruits or the vegetables to be even before harvest is more important. Therefore, a simple and non-invasive detecting technology for an instant detection of the fruits or vegetables anywhere at any time, is very important.

In view of the aforementioned demerit of the prior art, how to provide a simple, accurate, real-time, convenient, and non-invasive sweetness detecting apparatus and method thereof, is not only important for the fruits or the vegetables, but also a good news for the farmers and the related supply chain.

SUMMARY OF THE INVENTION

To the technical problems above-mentioned, the objects of the present invention are to provide a non-invasive detecting apparatus for fruits or vegetables, and a ranking method thereof. The non-invasive detecting apparatus can sense a sugar content of the fruits or the vegetables by gently heating the fruits or the vegetables. Accordingly, the non-invasive detecting apparatus can also determine the sweetness or the sour grade by the sensed sugar content, and helps the farmers or the related supply chains to rank the fruits or the vegetables.

In one perspective, the present invention provides a non-invasive detecting apparatus for fruits or vegetables, which includes: a sensing module, located in the non-invasive detecting apparatus, a heater, located in the sensing module and configured to operably heat the fruits or the vegetables; a temperature sensor, located in the sensing module and configured to operably sense a temperature variation level of the fruits or the vegetables, after heating the fruits or the vegetables by the heater; a processor, electrically coupled to the heater and the temperature sensor; a power supply, electrically coupled to the processor for supplying a power to the processor; and a user control unit, electrically coupled to the processor, for turning on, turning off, or setting the heater.

In one embodiment of the present invention, the non-invasive detecting apparatus for fruits or vegetables further including a display unit, which is electrically coupled to the processor for displaying the temperature variation level of the fruits or the vegetables.

In one embodiment of the present invention, the non-invasive detecting apparatus for fruits or vegetables, further including a communication unit, which is electrically coupled to the processor, for receiving a signal from a remote device, or transmitting another signal to the remote device.

In one embodiment of the present invention, a leaning surface of the heater on the fruits or the vegetables includes a dent region corresponding to the fruits or the vegetables. A leaning surface of the temperature sensor on the fruits or the vegetables includes another dent region corresponding to the fruits or the vegetables.

In one embodiment of the present invention, the heater is a gentle heater, which includes: a thermal resistor controlled heater, for heating a local region on the fruits or the vegetables; an air heater or an infrared heater, for heating a local region on the fruits or the vegetables, or heating all over the fruits or the vegetables; or a hot water soaking unit, for heating all over the fruits or the vegetables; wherein a temperature increase range by the gentle heater is preferably between 5 and 20 degrees Celsius. In one embodiment, the heater is not limited to the gentle heat; for example, the heater can be a micro heater.

In one embodiment of the present invention, the temperature sensor is an infrared thermographer.

In one perspective, the present invention provides a ranking method for the non-invasive detecting apparatus for fruits or vegetables, which includes: obtaining a weight of each of the fruits or the vegetables, and sorting the fruits or the vegetables according to the obtained weight; heating the fruits or the vegetables through a predetermined time period; sensing a temperature variation level of the fruits or the vegetables after heating the fruits or the vegetables; and ranking the fruits or the vegetables according to the temperature variation level.

In one embodiment of the present invention, the aforementioned step of heating the fruits or the vegetables is a step of gently heating the fruits or the vegetables, which includes: heating a local region on the fruits or the vegetables, under control of a thermal resistor; heating a local region on the fruits or the vegetables, or heating all over the fruits or the vegetables, by warming air or infrared; or heating the fruits or the vegetables by soaking all over the fruits or the vegetables in hot water; wherein a temperature increase range in the gently heating step is preferably between 5 and 20 degrees Celsius.

In one embodiment of the present invention, the aforementioned step of sensing the temperature variation level of the fruits or the vegetables after heating the fruits or the vegetables, includes: sensing a temperature variation of the fruits or the vegetables by an infrared thermographer, with mapping from the sensed temperature into corresponding infrared thermographic color.

In one embodiment of the present invention, the aforementioned step of ranking the fruits or the vegetables according to the temperature variation level, further includes: ranking the fruits or the vegetables according to: a highest sweetness, corresponding to a lowest temperature variation level; a medium sweetness, corresponding to a medium temperature variation level; and a lowest sweetness, corresponding to a highest temperature variation level.

BRIEF DESCRIPTION OF THE DRAWINGS

The application file contains at least one drawing executed in color. Copies of this patent application publication with color drawing(s) will be provided by the Office upon request and payment of the necessary fee.

DESCRIPTION OF THE PREFERRED EMBODIMENTS

Figure 1:
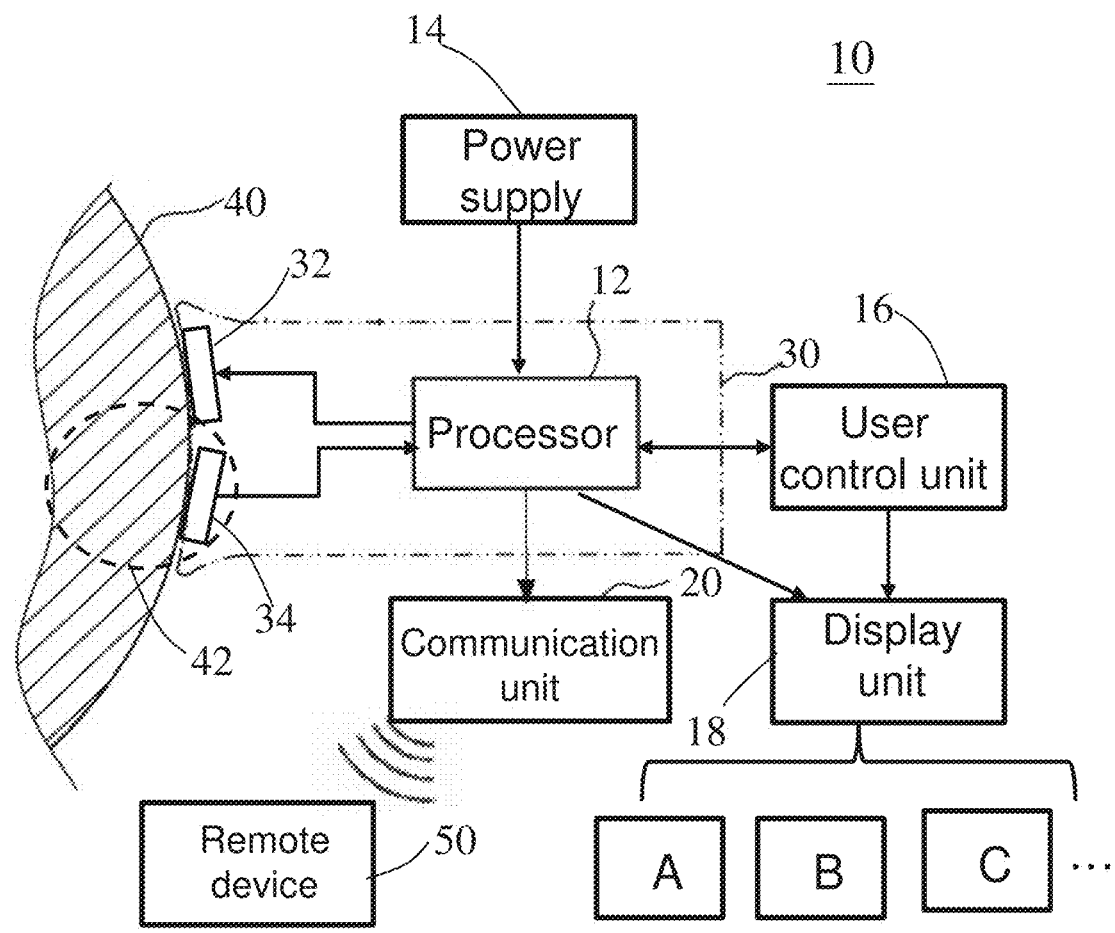
FIG. 1 shows a non-invasive detecting apparatus for fruits or vegetables according to one embodiment of the present invention.

The objectives, technical details, features, and effects of the present invention will be better understood with regard to the detailed description of the embodiments below, with reference to the drawings.

Generally, ingredients of the fruits or the vegetables include: water, sugar, organic acids, starch, and cellulose, which affect the sweetness and sour grade of the fruits or the vegetables. The ingredients of different kinds of fruits or vegetables are different. For example, the water content of the fruits is between 70% and 90%, and the sweetness resources of the fruits can includes sugar, glucose, fructose, etc. Different kinds of fruits have different sweetness resource compositions: apples and pears include fructose more; and berries and grapes include glucose and fructose more. No matter what kinds of sweetness resources are included in the fruits, the sweetness resources can all be considered as energy resources. For example, in one embodiment, the sweetness can be represented by Brix, which is defined by the amount of sucrose dissolved in an aqueous solution of 100 grams at 20 degrees Celsius.

One feature of the present invention is to determine the sugar content in the fruits or the vegetables, by a gently heating (non-invasive detecting step) to sense a temperature variation level of the fruits or the vegetables. Thereby, a sweetness of the fruits or the vegetables corresponding to the temperature variation level can be determined. The farmers or the related supply chains can accordingly rank the fruits or the vegetables according to the determined sweetness.

The algorithm of determining the sweetness or the sour grade of the fruit and vegetable of the invention is based on the physical property of heat capacity. When the fruits with a high heat capacity are heated, the temperature increase of the fruits during the heating process is lower because of an influence of the high heat capacity. Or, when the fruits with a low heat capacity are heated, the temperature increase of the fruits during the heating process is higher because of an influence of the low heat capacity. The relation between the heat capacity and a capability of absorbing heat (or heat dissipation) is: an object with higher heat capacity owns a higher capability of absorbing heat (or heat dissipation), and the temperature increase of the fruits during the heating process is lower; or, an object with lower heat capacity owns a lower capability of absorbing heat (or heat dissipation), and the temperature increase of the fruits during the heating process is higher.

For example, two materials A and B respectively, have heat capacities of 4200 J/(kg·K) and 2100 J/(kg·K). That is, the heat capacity of the material A is two times of the material B. Based on same temperature increase value, the necessary heat for the material A is two times of the material B. In another perspective, when the material A and B receive the same heat energy quantity, the temperature increase of the material B is higher than the material A. Their relation can be illustrated as following formula:

$$C = \frac{E}{m \Delta T}$$

$C$: Heat capacity, International unit J/(kg·K)

$E$: Heat $m$: Mass $\Delta T$: Temperature difference

Referring first to one embodiment of FIG. 1, wherein a non-invasive detecting apparatus for fruits or vegetables 10 is shown, and the elements of the non-invasive detecting apparatus for fruits or vegetables 10 are shown as block diagrams. The non-invasive detecting apparatus for fruits or vegetables 10 includes: a sensing module 30 having a processor 12, a heater 32 and a temperature sensor 34, wherein the processor 12, the heater 32 and the temperature sensor 34 are all located in the non-invasive detecting apparatus 10, and the processor 12 is electrically coupled to the heater 32 and the temperature sensor 34; a power supply 14, electrically coupled to the processor 12 for supplying a power to the processor 12 (or any of the aforementioned electronic components); and a user control unit 16, electrically coupled to the processor 12, for turning on, turning off, or setting the heater 32. In one embodiment, the non-invasive detecting apparatus for fruits or vegetables 10 further includes a display unit 18, which can be a liquid crystal display electrically coupled to the processor 12 for displaying the sweetness, or displaying a ranking grade of the fruits or the vegetables 40 (for example, grade A, grade B, grade C, etc.).

Please keep referring to FIG. 1, the heater 32 and the temperature sensor 34 are disposed in the sensing module 30. The heater 32 can be configured to lean on a surface of the fruits or the vegetables 40 (directly or indirectly), to heat the fruits or the vegetables 40. The leaning surface of the heater 32 on the fruits or the vegetables 40 is preferably but not limited to a dent-shaped surface. The method of heating the fruits or the vegetables 40 can be a means of gently heating the fruits or the vegetables, which includes but is not limited to: a micro-heating method or a thermistor-heating (thermal resistor heating) method for heating a part of (ex: the local region 42) or whole of the fruits or the vegetables 40; a hot-air heating, warm-air heating or an infrared heating method for heating apart of (ex: the local region 42) or whole of the fruits or the vegetables 40; or a hot-water soaking or warm-water soaking method for heating a part of (ex: the local region 42) or whole of the fruits or the vegetables 40. The temperature sensor 34 is configured to operably lean on the surface of the fruits or the vegetables 40, for sensing the temperature or the change of temperature of the fruits or the vegetables 40. The leaning surface of the temperature sensor 34 on the fruits or the vegetables 40 is preferably but not limited to another dent-shaped surface. The power supply 14 can includes battery, battery set, rechargeable battery, USB power supply, or wireless charging device. In one embodiment, the temperature sensor 34 can be an infrared thermographer, which is capable of mapping from the sensed temperature into corresponding infrared thermographic color.

Figure 2:
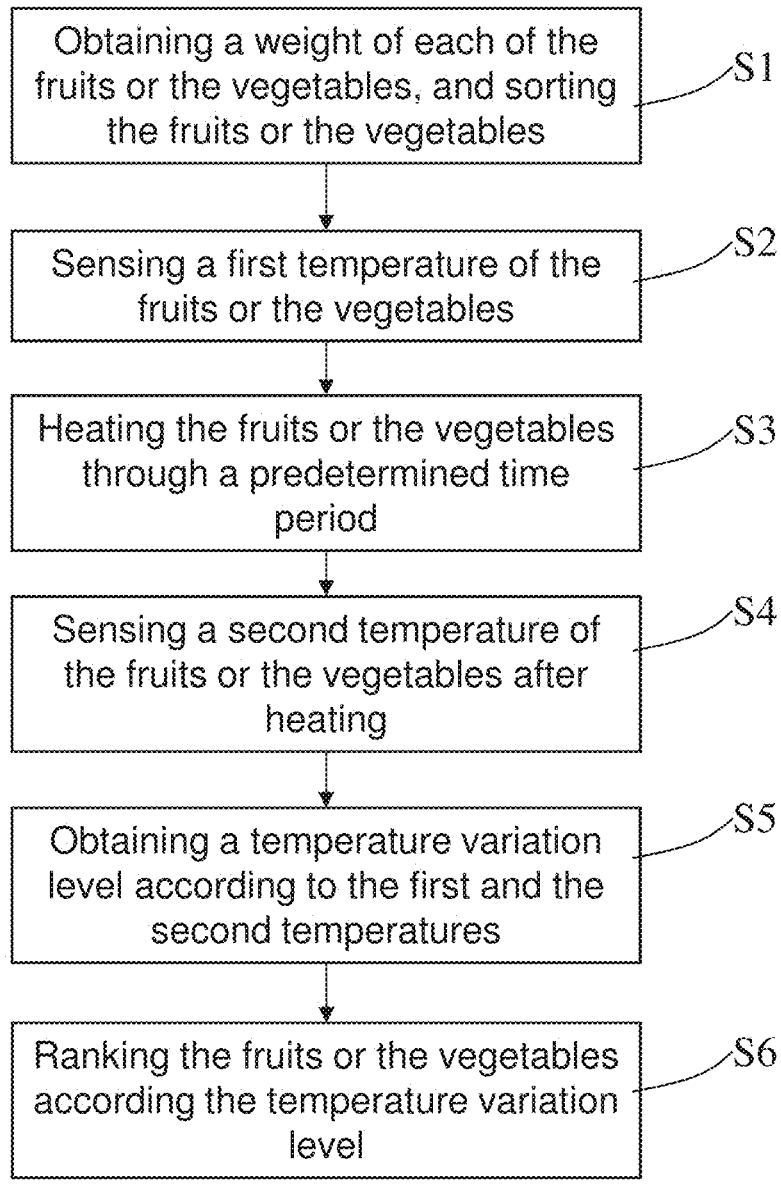
FIG. 2 shows a flowchart of a non-invasive detecting and ranking method, according to one embodiment of the present invention.

FIG. 2 shows a flowchart of a non-invasive detecting and ranking method, according to one embodiment of the present invention. The non-invasive detecting and ranking method include: obtaining a weight of each of the fruits or the vegetables, and sorting the fruits or the vegetables according to the obtained weight or in the obtained range of weight (step S1); sensing a first temperature of the fruits or the vegetables before heating the fruits or the vegetables, wherein the first temperature is at room temperature usually between 20 to 25 degrees Celsius (step S2); heating the fruits or the vegetables through a predetermined time period (step S3); sensing a second temperature of the fruits or the vegetables after heating the fruits or the vegetables (step S4); obtaining a temperature variation level according to the first and the second temperatures (step S5); and ranking the fruits or the vegetables according to the temperature variation level (step S6).

In the aforementioned step S1, the fruits or the vegetables are the same kind of fruits or the vegetables. The weight of each of the fruits or the vegetables is first obtained, and then the fruits or the vegetables are sorted and marked according to the obtained weight. The step S1 is to control the influence of the obtained mass on sensing the heat capacity according to the heat capacity formula. That is, the mass factor should be fixed so that the effect of mass factor on heat capacity can be eliminated. Therefore, the sensing result of each of the fruits or the vegetables can be accordingly adjusted or adjusted with weighting for getting a correct sensing or detecting result. In the step S3, the fruits or the vegetables are preferably gently heated, wherein the gentle heating includes but is not limited to: heating a local region 42 on the fruits or the vegetables 40, under control of a thermal resistor; heating a local region 42 on the fruits or the vegetables 40, or heating all over the fruits or the vegetables 40, by warming air or infrared; or heating the fruits or the vegetables by soaking all over the fruits or the vegetables in hot water. Importantly, the heating in the step S3 can be merely a gently heating step to make the temperature of the fruits or the vegetables 40 increase. For example, the temperature increase is between 5 and 20 degrees Celsius. According to the present invention, it is not necessary to make the temperature of the fruits or the vegetables 40 increase in a large scale, to avoid a negative impact on the fruits or the vegetables 40. In the step S5, a difference between the first and second temperatures, is divided by the predetermined time period, to obtain the temperature variation level. For example, when the first temperature is the room temperature, the second temperature is a key for deciding to the temperature variation level (that is, user can detect a temperature variation only according to the second temperature). The predetermined time period is preferred in minutes scale. Or, the step of sensing the temperature variation level of the fruits or the vegetables 40, includes: sensing a temperature variation of the fruits or the vegetables 40 according to an infrared thermographic technology (for example, by the infrared thermographer). For example, the first temperature of the fruits or the vegetables 40 being at the room temperature; heating the fruits or the vegetables 40 through the predetermined time period; and sensing the temperature increase (the second temperature) of the fruits or the vegetables 40 by the infrared thermographer according to infrared thermographic color change. Thus, the temperature variation level of the fruits or the vegetables 40 can be obtained. In the step S6, the fruits or the vegetables 40 can be ranked according to the temperature variation level obtained in the step S5. For example, the fruits or the vegetables 40 of the grade A, corresponding to a lowest temperature variation level for representing a highest sweetness; the fruits or the vegetables 40 of the grade B, corresponding to a medium high temperature variation level, for representing a medium high highest sweetness; the fruits or the vegetables 40 of the grade C, corresponding to a low medium temperature variation level, for representing a low medium sweetness (or slightly sweet); and the fruits or the vegetables 40 of the grade D, corresponding to a highest temperature variation level, for representing a lowest sweetness (or not sweet).

The infrared thermographic image in the aforementioned step S5, whose principle is: every object has its own natural electromagnetic radiation for radiating heat, and the intensity of electromagnetic radiation is distributed with respect to the wave length according to the temperature distribution of the object. For example, when an animal, a plant, or a human body is sensed by an infrared photographic image, wherein the obtained infrared photographic color in the infrared photographic image is usually concentrated in the infrared wavelength range. The higher the temperature of the object is, the corresponding infrared photographic color is yellow red biased. The lower the temperature of the object is, the corresponding infrared photographic color is blue biased. As shown in a color temperature table in FIG. 3B, the corresponding infrared photographic wavelength color of 20 degrees Celsius is red, and the corresponding infrared photographic wavelength color between 31-33 degrees Celsius is yellow, and the corresponding infrared photographic wavelength color above 33 degrees Celsius is incandescent. In one embodiment, the color temperature table according to the present invention can for example but not limited to the color temperature table in FIG. 3B; for example, the temperature of the object corresponding to the infrared photographic wavelength color between different colors can be adjusted (color shift).

Figure 3A:
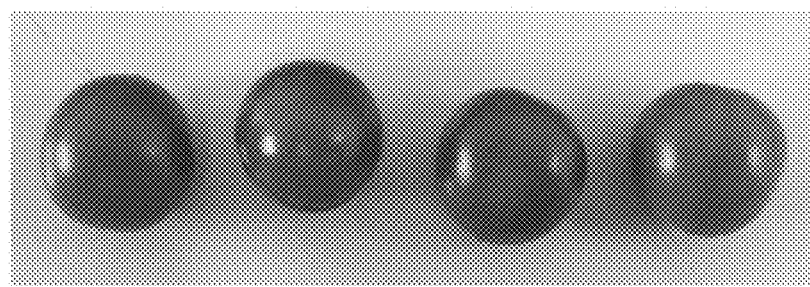
FIG. 3A shows a plurality of fruits for detecting sweetness by the non-invasive detecting apparatus according to the present invention.
Figure 3B:
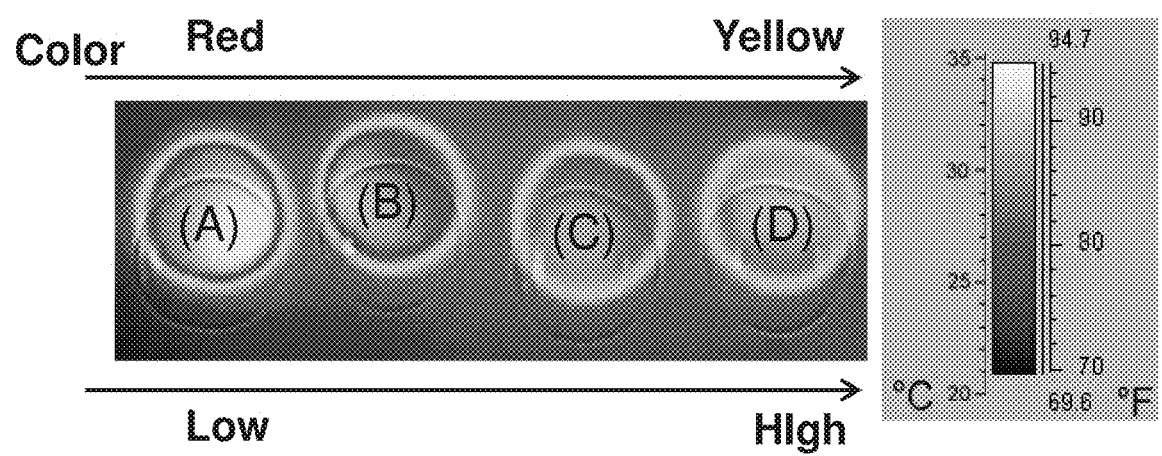
FIG. 3B shows an infrared thermographic image corresponding to the fruits in FIG. 3A.

Please refer to FIGS. 3A and 3B, wherein FIG. 3A shows one embodiment of the fruits applied to the non-invasive detecting apparatus of the present invention, and FIG. 3B shows the infrared photographic image corresponding to FIG. 3A. In the right side of FIG. 3B, the color temperature table is shown. In the aforementioned gently heating step of the present invention, how the heat capacity influences the temperature increase is shown in FIGS. 3A and 3B. In FIG. 3A, there is no necessary cut or other abnormal indication on the surface of the fruits. FIG. 3B shows infrared photographic image corresponding to the fruits of FIG. 3A after the gently heating step. As shown in FIG. 3B, every fruit has different temperature variations after the gently heating step. The fruits can be ranked into at least four grades: the fruit(s) having the highest temperature corresponds to the grade D; the fruit(s) having the high temperature corresponds to the grade C; the fruit (s) having the low temperature corresponds to the grade B; and the fruit (s) having the lowest temperature corresponds to the grade A. The higher the temperature increases, the lower the capacity influences (usually a lower sweetness). Or, the lower the temperature increases, the higher the capacity influences (usually a higher sweetness). For example, the grade A represents the highest sweetness; the grade B represents the medium high sweetness; the grade C represents the low medium sweetness; and the grade D represents the lowest sweetness. In this embodiment, according to the temperature increases, the sweetness of the fruits can be ranked by into distinct grades.

Importantly, any temperature variation can be used to rank the fruits or the vegetables. In the aforementioned embodiment, the fruits are heated for ranking purpose. However, according to the heat capacity formula, the heat capacity change is based on the mass and the supplied heat. As shown in FIG. 2, the fruits are first sorted according to their weights, and then the fruits are gently heated. The heat capacity corresponds to the heat storing capability of the object. When the heat storing capability is good, the heat conduction speed is slow. The sweetness can be determined by heating and sensing the heat transfer. Through heating the fruits or the vegetables at a constant temperature, the temperature variation of the fruits or the vegetables can be sensed. The temperature variation can be used to rank the fruits or the vegetables under different weight classification.

In one embodiment, the non-invasive detecting apparatus for fruits or vegetables 10 can further include a communication unit 20 (FIG. 1), which is electrically coupled to the processor 12, for receiving a signal from a remote device 50, or transmitting another signal to the remote device 50. In one embodiment, The remote device 50 is preferably a server or a communication terminal device.

According to the present invention, the non-invasive detecting apparatus for fruits or vegetables 10 has the benefits of simple design, easy and quick detecting step, and a wide application domain. When the fruits and vegetables are planted, before harvest, after harvest, or in a shipment, the non-invasive detecting apparatus for fruits or vegetables 10 and the ranking method of the present invention can be utilized to detect the fruits or the vegetables.

The present invention has been described in considerable detail with reference to certain preferred embodiments thereof. It should be understood that the description is for illustrative purpose, not for limiting the scope of the present invention. For example, the temperature variation level can be measured or obtained by a temperature decrease. Those skilled in this art can readily conceive variations and modifications within the spirit of the present invention.

What is claimed is:

1. A ranking method of a non-invasive detecting apparatus for fruits or vegetables, comprising:
    heating the fruits or the vegetables through a predetermined time period;
    sensing a temperature variation level of the fruits or the vegetables after heating the fruits or the vegetables; and
    ranking sweetness of the fruits or the vegetables, according to the temperature variation level, wherein the sweetness of the fruits or the vegetables is ranked according to the measured temperature variation level.

2. A non-invasive detecting apparatus for fruits or vegetables used for the ranking method of claim 1, comprising:
    a heater, configured to operably heat the fruits or the vegetables;
    a temperature sensor, configured to operably sense the temperature variation level of the fruits or the vegetables, after heating the fruits or the vegetables by the heater;
    a processor, electrically coupled to the heater and the temperature sensor;
    a power supply, electrically coupled to the processor for supplying a power to the processor; and
    a user control unit, electrically coupled to the processor, for turning on, turning off, or setting the heater.

3. The non-invasive detecting apparatus for fruits or vegetables of claim 2, further comprising a display unit, which is electrically coupled to the processor for displaying the temperature variation level of the fruits or the vegetables.

4. The non-invasive detecting apparatus for fruits or vegetables of claim 2, further comprising a communication unit, which is electrically coupled to the processor, for receiving a signal from a remote device, or transmitting another signal to the remote device.

5. The non-invasive detecting apparatus for fruits or vegetables of claim 2, wherein the fruits or the vegetables are heated by leaning the heater on a surface of the fruits or the vegetables, and a leaning surface of the heater on the fruits or the vegetables includes a first dent-shaped surface corresponding to the fruits or the vegetables; or a leaning surface of the temperature sensor on the fruits or the vegetables includes a second dent-shaped surface corresponding to the fruits or the vegetables.

6. The non-invasive detecting apparatus for fruits or vegetables of claim 2, wherein the heater is a gentle heater, which includes: a thermal resistor controlled heater, an air heater or an infrared heater, or a hot water soaking unit, for heating a part of or all over the fruits or the vegetables; wherein a temperature increase range by the gentle heater is between 5 and 20 degrees Celsius.

7. The non-invasive detecting apparatus for fruits or vegetables of claim 2, wherein the temperature sensor is an infrared thermographer.

8. The ranking method of claim 1, further comprising: before heating the fruits or the vegetables, obtaining a weight of each of the fruits or the vegetables, and sorting the fruits or the vegetables according to the obtained weight.

9. The ranking method of claim 1, wherein the aforementioned step of heating the fruits or the vegetables, is a step of gently heating the fruits or the vegetables, which includes: heating a local region on the fruits or the vegetables, under control of a thermal resistor; heating a local region on the fruits or the vegetables, or heating all over the fruits or the vegetables, by warming air or infrared; or heating the fruits or the vegetables by soaking all over the fruits or the vegetables in hot water; wherein a temperature increase range in the gently heating step is between 5 and 20 degrees Celsius.

10. The ranking method of claim 1, wherein the aforementioned step of sensing the temperature variation level of the fruits or the vegetables after heating the fruits or the vegetables, includes: sensing a temperature variation of the fruits or the vegetables by an infrared thermographer, with mapping from the sensed temperature into corresponding infrared thermographic color.

11. The ranking method of a non-invasive detecting apparatus for fruits or vegetables, comprising:

heating the fruits or the vegetables through a predetermined time period;

sensing a temperature variation level of the fruits or the vegetables after heating the fruits or the vegetables; and ranking sweetness of the fruits or the vegetables, according to the temperature variation level, wherein the sweetness of the fruits or the vegetables is ranked according to the measured temperature variation level, wherein the aforementioned step of ranking the sweetness of the fruits or the vegetables according to the temperature variation level, further includes: the fruits or the vegetables are ranked according to: a first grade, corresponding to a lowest temperature variation level for representing a highest sweetness; a second grade, corresponding to a temperature variation level higher than the first grade, for representing a second highest sweetness; a third grade, corresponding to a temperature variation level higher than the second grade, for representing a third highest sweetness; and a fourth grade, corresponding to a highest temperature variation level (higher than the third grade), for representing a lowest sweetness.

* * * * *